(12) United States Patent
Cinader, Jr.

(10) Patent No.: US 10,307,221 B2
(45) Date of Patent: Jun. 4, 2019

(54) ORTHODONTIC TREATMENT MONITORING BASED ON REDUCED IMAGES

(75) Inventor: David K. Cinader, Jr., Walnut, CA (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 442 days.

(21) Appl. No.: 12/808,196

(22) PCT Filed: Dec. 16, 2008

(86) PCT No.: PCT/US2008/086985
§ 371 (c)(1),
(2), (4) Date: Jun. 15, 2010

(87) PCT Pub. No.: WO2009/085752
PCT Pub. Date: Jul. 9, 2009

(65) Prior Publication Data
US 2010/0260405 A1     Oct. 14, 2010

Related U.S. Application Data

(60) Provisional application No. 61/015,934, filed on Dec. 21, 2007.

(51) Int. Cl.
G06K 9/00 (2006.01)
A61C 7/00 (2006.01)

(52) U.S. Cl.
CPC ............... *A61C 7/00* (2013.01); *A61C 7/002* (2013.01)

(58) Field of Classification Search
CPC .. A61C 7/00; A61C 7/002; A61C 7/12; A61C 7/146; A61C 13/0004; G16H 20/40
(Continued)

(56) References Cited

U.S. PATENT DOCUMENTS 5,975,893 A    11/1999    Chishti et al.
6,371,761 B1    4/2002    Cheang et al.
(Continued)

FOREIGN PATENT DOCUMENTS

WO    WO 00/25677    5/2000
WO    WO 2007/084727    7/2007

OTHER PUBLICATIONS

International Search Report PCT/US2008/086985 dated Jul. 10, 2010; 5 pgs.

*Primary Examiner* — Hiep V Nguyen

(57) ABSTRACT

The present invention provides digitally driven methods to conveniently and efficiently monitor and evaluate the positions of a patient's teeth during the course of orthodontic treatment. In an exemplary embodiment, an initial set of 3D digital data representing a patient's dental structure is provided by means of an X-ray radiograph and/or an intraoral scan. Then during the course of treatment, a reduced image representing part of the dental structure may be quickly provided using a bite plate or a low resolution intraoral scan. A three-dimensional (3D) image of the full dental structure is subsequently rendered or 'reconstructed' by registering elements of the initial image with corresponding elements of the reduced image. By reconstructing the dental structure from the reduced image, the treating professional can provide a precise, manipulable 3D image of the patient's complete dental structure for diagnostic and treatment planning purposes. Other aspects include methods of using these data to compare actual and target teeth positions to evaluate the progress of treatment and suggest revisions to the specification of an orthodontic appliance.

19 Claims, 8 Drawing Sheets

(58) Field of Classification Search
USPC .......................................................... 382/132
See application file for complete search history.

(56) References Cited

U.S. PATENT DOCUMENTS

| | | | |
|---|---|---|---|
| 6,632,089 B2 | 10/2003 | Rubbert et al. | |
| 6,845,175 B2* | 1/2005 | Kopelman et al. | 382/154 |
| 7,020,963 B2 | 4/2006 | Cleary et al. | |
| 7,027,642 B2* | 4/2006 | Rubbert et al. | 382/154 |
| 7,188,421 B2 | 3/2007 | Cleary et al. | |
| 7,234,937 B2 | 6/2007 | Sachdeva et al. | |
| 7,245,750 B2 | 7/2007 | Hultgren et al. | |
| 7,245,753 B2* | 7/2007 | Squilla et al. | 382/128 |
| 7,653,455 B2* | 1/2010 | Cinader, Jr. | 700/119 |
| 2003/0021453 A1 | 1/2003 | Weise et al. | |
| 2004/0029068 A1 | 2/2004 | Sachdeva et al. | |
| 2004/0142298 A1 | 7/2004 | Taub et al. | |
| 2005/0074717 A1 | 4/2005 | Cleary et al. | |
| 2005/0192835 A1* | 9/2005 | Kuo et al. | 705/2 |
| 2006/0223021 A1 | 10/2006 | Cinader, Jr. et al. | |
| 2006/0223031 A1 | 10/2006 | Cinader, Jr. et al. | |
| 2007/0031791 A1 | 2/2007 | Cinader, Jr. et al. | |
| 2007/0141525 A1 | 6/2007 | Cinader, Jr. et al. | |
| 2007/0172101 A1 | 7/2007 | Kriveshko et al. | |
| 2007/0207437 A1 | 9/2007 | Sachdeva et al. | |
| 2007/0232961 A1 | 10/2007 | Wen | |
| 2008/0233531 A1 | 9/2008 | Raby et al. | |
| 2008/0305458 A1 | 12/2008 | Lemchen | |

* cited by examiner

ORTHODONTIC TREATMENT MONITORING BASED ON REDUCED IMAGES

CROSS REFERENCE TO RELATED APPLICATIONS

This application is a national stage filing under 35 U.S.C. 371 of PCT/US2008/086985, filed Dec. 16, 2008, which claims the benefit of U.S. Provisional Application No. 61/015,934, filed Dec. 21, 2007, the disclosures of which are incorporated by reference in their entireties herein.

1. FIELD OF THE INVENTION

The present invention is generally in the field of orthodontic treatment. More particularly, the present invention is directed to methods of orthodontic treatment monitoring and planning.

2. DESCRIPTION OF THE RELATED ART

Orthodontics is the area and specialty of dentistry associated with the supervision, guidance, and correction of teeth positions in the mouth. This is achieved by the application and/or re-direction of forces to teeth to bring them into proper positions relative to each other as well as facial bones such as the jawbone.

In one common type of treatment, tiny slotted appliances called brackets are affixed to a patient's teeth and a resilient archwire is placed in the slot of each bracket. The ends of the archwire are provided in appliances called buccal tubes, which are affixed to the patient's molar teeth. The archwire is deflected when placed in the mouth, but subsequently imparts continuous forces to urge the teeth to proper locations as it returns to its original shape. The brackets, buccal tubes, and archwire are often referred to collectively as "braces".

Active orthodontic therapy typically lasts between one to three years, from the time appliances are first bonded to the teeth to the time they are debonded at the conclusion of treatment. While the movement of teeth may occur throughout the course of treatment, movement does not usually occur in a smooth continuous fashion. Sometimes there are "bottlenecks" that impede, or even stall, tooth movement. For example, certain teeth may need to be moved out of the way to create space for other teeth. Delays may also develop because of anchorage loss or undesirable tooth movement that must be remedied before proceeding further. Moreover, certain teeth may simply move slower than others, based on the unique biology of each patient's dental structure.

The treating professional, typically an orthodontist, can anticipate some of these challenges when formulating a treatment plan for the patient. As a starting point, the treating professional provides a three dimensional image of the malpositioned teeth, often with the assistance of X-rays and/or plaster study models. The treating professional then contemplates a mental image corresponding to the desired finished positions of the teeth, and foresees a treatment path to arrive at that state. The treatment plan hence acts as a "roadmap" that identifies the sequence of intermediate and final goals that lead the patient from the maloccluded state to the finished state. The treatment plan may also include the expected timelines for accomplishing each of the intermediate and final goals, based on the experience and expertise of the treating professional.

Despite the diligence and best intentions of the treating professional, however, it is rare that the actual treatment progresses exactly according to the treatment plan. Unplanned adjustments are often required; for example, the treating professional may place additional bends in the archwire or re-position appliances on one or more teeth to achieve a proper treatment result. These adjustments are the result of continual evaluations as to the progress of treatment, and these evaluations are, in turn, based on what is seen by the treating professional during routine inspections of the patient's teeth. This process is both subjective and inherently imprecise. The oral environment makes it difficult if not impossible for a human being, unassisted, to develop a visual three dimensional image of the patient's dental structure because of limitations in human sight and the physical structure of the patient's mouth. Furthermore, the roots of the teeth are not readily visible, making it difficult to incorporate hidden aspects of the dentition, such as teeth roots, into mid-course treatment planning.

SUMMARY OF THE INVENTION

Due to the limitations in conventional orthodontic treatment monitoring methods described above, the process of providing precise relative positions of teeth during treatment is often time consuming and inefficient. The present invention provides methods to conveniently and efficiently monitor and evaluate the positions of a patient's teeth during the course of orthodontic treatment using digital information. In an exemplary embodiment, an initial set of digital data representing a patient's dental structure is provided by an X-ray radiograph and/or intraoral scan. Then during the course of treatment, a reduced image representing part of the dental structure may be conveniently provided using a bite plate impression or an ultra-fast low resolution intraoral scanner. A three-dimensional (3D) image of the full dental structure is subsequently derived or "reconstructed" by aligning or registering elements of the initial image with corresponding elements of the reduced image. By digitally reconstructing the dental structure using elements from both images, the treating professional can provide a precise, current and manipulable 3D image of the patient's complete dental structure for diagnostic and treatment planning purposes.

This invention provides a method for deriving full 3D images of teeth positions and orientations during treatment, evaluating treatment progress, and calculating adjustments to an orthodontic appliance with particular advantages to both the treating professional and patient. First, by leveraging a full set of dental data already acquired at the outset of treatment, only small portions of the dental data are needed to reconstruct the current position of the entire dental structure. While taking a full dental impression or a high-resolution intraoral scan is time-consuming and uncomfortable to the patient, a bite register can be taken in seconds and scanned offline, with minimal patient discomfort. As a further advantage, normally hidden features of the dental structure such as the roots can be integrated into the current 3D image without the need to perform additional radiographs. This can be especially useful when temporary anchorage devices (TADs) are involved, since these imaging techniques can help a treating professional visualize the positions of TADs relative to the teeth roots. Finally, by providing full detailed images of the teeth including their roots, this method can be useful in diagnosing treatment issues and suggesting mid-course corrections to an orthodontic appliance such as an archwire or other appliance(s).

In further detail, an aspect of the invention is directed to a method of deriving an image of a dental arrangement of a patient including the steps of providing a first digital image representing a first dental arrangement, providing a second digital image representing a second dental arrangement, wherein the second digital image is a reduced image when compared to the first digital image and wherein at least one tooth in the second dental arrangement is in a different position than the corresponding tooth in the first dental arrangement, deriving a third digital image representing the second dental arrangement by registering at least one element of the first digital image with at least one corresponding element of the second digital image, wherein the third digital image is a supplemented image when compared to the second digital image.

Another aspect is directed to a method of comparing dental arrangements of a patient including the steps of providing a first digital image representing an first dental arrangement, deriving a target digital image representing a target dental arrangement, providing a second digital image representing a second dental arrangement, wherein the second digital image is a reduced image compared to the first digital image and wherein at least one tooth in the second dental arrangement is in a different position than the corresponding tooth in the first dental arrangement, and deriving a third digital image representing the second dental arrangement by registering at least one element of the first digital image with at least one corresponding element of the second digital image, wherein the third digital image is a supplemented image when compared to the second digital image.

Another aspect is directed to a method of specifying an orthodontic appliance including the steps of providing a proposed specification of an orthodontic appliance, providing a first digital image representing a first dental arrangement associated with the orthodontic appliance, deriving a target digital image representing a target dental arrangement by virtually moving teeth in the first dental arrangement to desired positions, providing a second digital image representing a second dental arrangement, wherein the second digital image is a reduced image when compared to the first digital image and wherein at least one tooth in the second dental arrangement is in a different position than the corresponding tooth in the first dental arrangement, registering at least one element of the target digital image to at least one corresponding element of the second digital image to derive a transformation matrix, and revising the proposed specification of the orthodontic appliance based in part on the transformation matrix.

Still another aspect is directed to a software program that carries out a method to derive an image of a dental arrangement of a patient including the steps of providing a first digital image representing a first dental arrangement, providing a second digital image representing a second dental arrangement, wherein the second digital image is a reduced image when compared to the first digital image and wherein at least one tooth in the second dental arrangement is in a different position than the corresponding tooth in the first dental arrangement, and deriving a third digital image representing the second dental arrangement by registering at least one element of the first digital image with at least one corresponding element of the second digital image, wherein the third digital image is a supplemented image when compared to the second digital image.

Yet still another aspect is directed to a system comprising a computing device and a software program executing on the computing device, wherein the software program includes a rendering engine that generates a first digital image representing a first dental arrangement and generates a second digital image representing a second dental arrangement, wherein the second digital image is a reduced image when compared to the first digital image and wherein at least one tooth in the second dental arrangement is in a different position than the corresponding tooth in the first dental arrangement, and a registration module that registers at least one element of the first digital image with at least one corresponding element of the second digital image to derive a third digital image representing the second dental arrangement, wherein the third digital image is a supplemented image when compared to the second digital image.

Further embodiments disclosed herein include providing the first digital image using a procedure such as light-based scanning, contact probing, active wavefront sampling, X-ray radiography, magnetic resonance imaging, ultrasound imaging and computerized tomography and providing the second digital image by scanning a bite impression, performing a low resolution scan, or performing a partial intraoral scan. Other embodiments include the steps of registering elements that include teeth, appliances bonded to the teeth, and non-bonded appliances such as temporary anchorage devices.

DEFINITIONS

Figure 1:
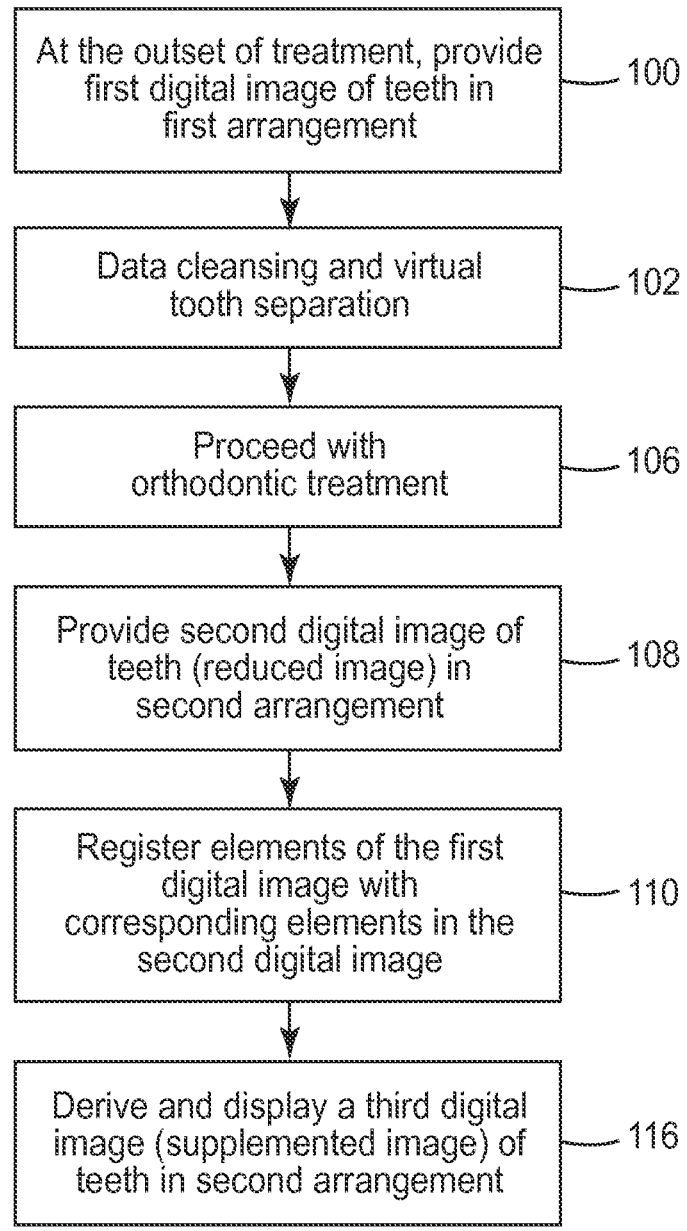
FIG. 1 is a block diagram describing some of the steps that are followed in monitoring an orthodontic treatment.

As used herein:

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

DETAILED DESCRIPTION OF THE PREFERRED EMBODIMENTS

The present invention is broadly directed in several embodiments to the registration of digital images provided at different times during treatment in order to provide new images that assist in orthodontic treatment monitoring and other associated applications. More particularly, one aspect of this invention is directed to registering elements from a first digital image with corresponding elements in a second, reduced digital image to derive these new images. Three embodiments of the invention, a Treatment Monitoring workflow, Treatment Evaluation workflow, and Appliance Revision workflow, are detailed in the flowcharts shown in FIGS. 1-3, respectively. Each of these workflows, in turn, can be sub-divided into several basic steps, which include Initial Image Acquisition, Data Processing, Treatment and Reduced Image Acquisition, Registration, and Application. In the following sections, each of these steps shall be examined in turn, bearing in mind that the invention may be represented by less than all of the illustrated steps, more than the illustrated steps, and/or steps in a different order than the ones shown.

Initial Image Acquisition

As used herein, "dental arrangement" is defined as a set or subset of one or more of the following—tooth elements (such as crowns and roots), gingiva, bone, bonded appliances, implanted appliances and other associated anatomical structures—positioned in three-dimensional (3D) space and associated with a patient at a particular time during treatment. The term "digital image" may include digital data that represents, defines or renders a viewable 3D image, or the image itself. In the examples below, the terms "digital image" and "digital data" are used interchangeably. Digital images can be stored, processed, and/or communicated using a back office server or workstation, such as a general purpose computing device having a processor capable of manipulating digital images, a user interface, and a display to allow a user to view digital images. The computing device further includes memory that is capable of storing multiple sets of digital images and fully accessible to software running on the computing device.

The Treatment Monitoring, Treatment Evaluation, and Appliance Revision workflows each begin with the acquisition of a digital image representing a patient's dental structure. In this first step, designated as block 100 in FIGS. 1-3, a first digital image of a patient's dental arrangement is provided and stored on a local or remote computing device. The digital image may represent the entire dental structure of a patient, just the upper or lower arch, or only a portion of one or both arches. A digital image representing only a portion of a patient's dental structure may be desired, for example, in cases in which treatment monitoring is sought for some but not all of the teeth. Optionally, the first digital image is provided at the outset of orthodontic treatment, for example immediately prior to or immediately after, the bonding or placement of orthodontic appliances onto the teeth. In some embodiments, the first digital image shows not only the patient's teeth but also the 3D shapes of brackets or other orthodontic appliances associated therewith. The geometric features of orthodontic appliances can provide landmarks for registering images with each other, as will be described later.

In some embodiments, the first digital image (block 100) may be provided using a hand-held intra-oral scanner such as the intra-oral scanner using active wavefront sampling developed by Brontes Technologies, Inc. (Lexington, Mass.) and described in PCT Publication No. WO 2007/084727 (Boerjes, et al.). Alternatively, other intra-oral scanners or intra-oral contact probes may be used. As another option, the first digital image (block 100) may be provided by scanning a negative impression of the patient's teeth. As still another option, the first digital image (block 100) may be provided by imaging a positive physical model of the patient's teeth or by using a contact probe on a model of the patient's teeth. The model used for scanning may be made, for example, by casting an impression of a patient's dentition from a suitable impression material such as alginate or polyvinylsiloxane (PVS), pouring a casting material (such as orthodontic stone or epoxy resin) into the impression, and allowing the casting material to cure. Any suitable scanning technique may be used for scanning the model, including X-ray radiography, laser scanning, computed tomography (CT), magnetic resonance imaging (MRI), and ultrasound imaging. Other possible scanning methods are described in U.S. Patent Publication No. 2007/0031791 (Cinader et al.).

In addition to providing digital images by scanning the exposed surfaces of the teeth, it is possible to image hidden features of the dentition, such as the roots of the patient's teeth and the patient's jaw bones. In some embodiments, the first digital image (block 100) is formed by providing several 3D images of these features and subsequently "stitching" them together. These different images need not be provided using the same imaging technique. For example, a digital image of teeth roots provided with a CT scan may be integrated with a digital image of the teeth crowns provided with an intraoral visible light scanner. Scaling and registering of 2D dental images with 3D dental images is described in U.S. Pat. No. 6,845,175 (Kopelman, et al.) and U.S. Patent Publication No. 2004/0029068 (Badura et al.). Issued U.S. Pat. No. 7,027,642 (Imgrund et al.) and U.S. Pat. No. 7,234,937 (Sachdeva, et al.) describe using techniques of integrating digital images provided from various 3D sources. Accordingly, the term "imaging" as it is used herein is not limited to normal photographic imaging of visually apparent structures, but includes imaging of dental structures that are hidden from view.

By integrating the image data of the roots along with that of the crowns, it is possible to monitor and/or simulate the relationships between the crowns and the roots as they move during treatment. Information that includes the tooth roots and jaws also enables a treating professional to provide a more comprehensive analysis of the teeth and surrounding bone structure. For example, an X-ray of the patient's jaws can assist in identifying teeth that are ankylosed (e.g. fused to the jawbone), while an MRI can provide information about the density of the patient's gum tissue. Moreover, information about the relationship between the patient's teeth and other cranial features allows accurate alignment of the teeth with respect to the rest of the head at each of the treatment steps. Similar information may be gathered on the positions of embedded temporary anchorage devices (TADs) or dental implants. By performing a scan or a combination of scans, these embedded devices can be imaged and mapped to a 3D image of the jawbone along with images of the adjacent teeth roots. Each of the scanning techniques described above may be carried out at the orthodontic office or alternatively at an off-site location.

Data Processing

Figure 2:
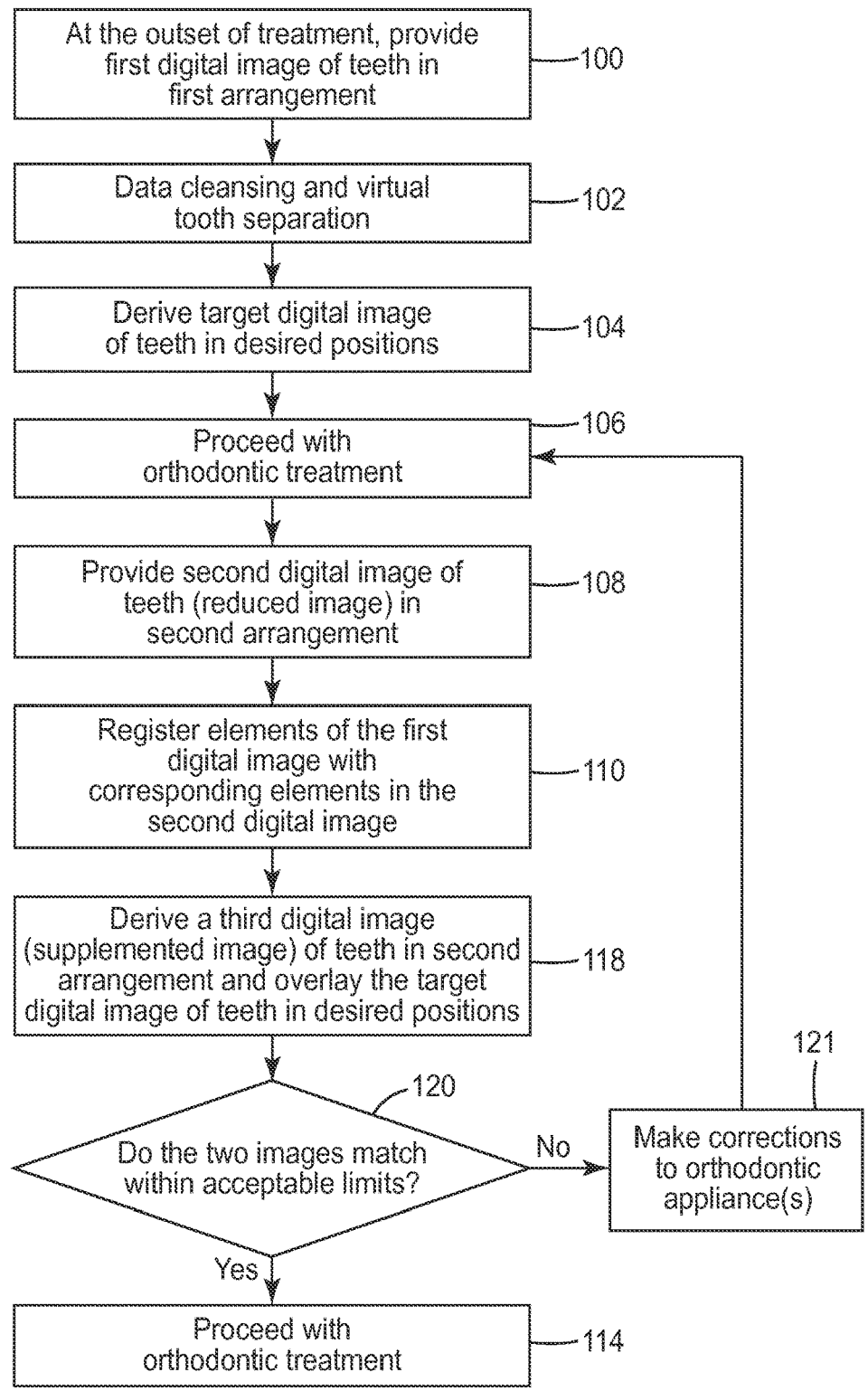
FIG. 2 is a block diagram describing some of the steps that are followed in the evaluation of an orthodontic treatment.
Figure 3:
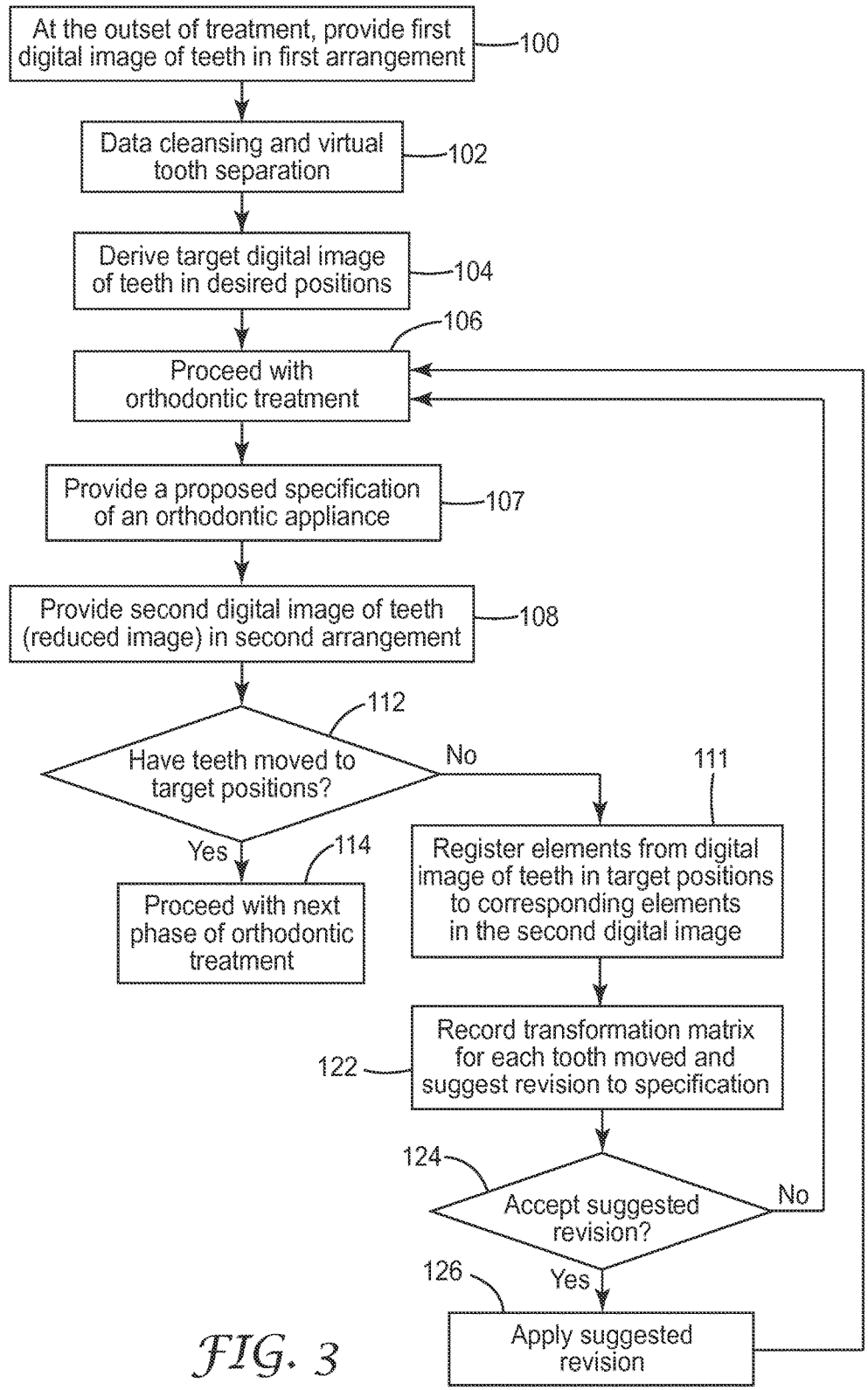
FIG. 3 is a block diagram describing some of the steps that are followed in revising the specification of an orthodontic appliance.

Block 102 in FIGS. 1-3 represents additional processing of the raw digital data acquired in block 100. For example, the raw data may be optionally "cleansed" by removing any data points that represent clear error or are unnecessary. For example, data files representing a tooth surface that include a data point significantly outside the normal expected geometrical relationship of adjacent data points could be fixed by data handling software to remove the erroneous data point. In addition, tooth data points that are missing could be added or estimated by data handling software to create realistic, smoothly curved shapes of teeth or the jawbone, as defined by the data points. In some embodiments, the digital data may be "surfaced", or converted from digital point clouds to 3D surfaces by modeling software from a provider such as Geomagic, Inc. (Research Triangle Park, N.C.). Depending on the types of scans taken, these surfaces may include surfaces which are hidden to the naked eye, such as surfaces representing teeth roots and the embedded tail portions of TADs. Surfaces representing hidden structures may be nested within surfaces representing the jawbone.

Also represented in block 102, the first digital image (block 100) is then virtually separated into discrete elements so that each tooth may be independently moved as a separate object. Optionally the teeth elements are also separated from the surrounding gingival tissue and bone, leaving only the floating 3D images of tooth crowns and roots. This can be performed using commercial software such as Geomagic Studio and/or Geomagic Dental (Geomagic Inc., Research Triangle Park, N.C.) running on the local or remote computing device and performed automatically or with the intervention of an operator. This procedure may similarly be carried out for structures that are not teeth. For example, implanted devices such as TADs can be virtually separated from the surrounding periodontal ligament and jawbone. Alternative methods that describe the separation of teeth into individual tooth objects are described in issued U.S. Pat. No. 6,632,089 (Rubbert et al.), U.S. Pat. No. 6,371,761 (Cheang et al.) and U.S. Pat. No. 7,245,750 (Cermak et al.).

In the Treatment Evaluation and Appliance Revision workflows, a target digital image of teeth in desired positions is additionally provided as indicated by block 104 of FIGS. 2 and 3. Preferably, the target digital image in block 104 is derived by virtually moving teeth in the first dental arrangement to desired positions and provides the same level of detail (e.g. same coverage and point density) as the first digital image in block 100. Herein, the "desired positions" may represent the final teeth positions at the conclusion of treatment, or alternatively represent positions of teeth upon reaching an intermediate treatment goal. In some embodiments, each of the desired tooth positions is in turn represented by a separate, independently movable element within the target digital image (block 104).

The digital image of the teeth in desired positions may be provided in a variety of ways. In one example, a treating professional may interact with the user interface of a computing device to view the three dimensional ("3D") virtual model and manually define the desired final positions of the patient's teeth. If the first digital image in block 100 already includes appliances bonded to the teeth, then the desired teeth positions in block 104 may be determined automatically by connecting a virtual archwire with the appliances and determining the final teeth positions based on the predicted movement of the archwire over time back to its normal relaxed configuration. In an alternative embodiment, providing the desired teeth positions (block 104) may include virtually translating an entire set of teeth on one jaw relative to the opposing jaw to simulate the effect of jaw surgery.

In the event that the first digital image in block 100 does not include appliances, then the desired teeth positions can be entirely derived using virtual appliances. For example, block 104 may include defining virtual appliances, virtually bonding the appliances to the tooth elements, and using a virtual archwire to move the tooth elements to desired positions. In one embodiment, the treating professional selects and places virtual appliances such as brackets and buccal tubes on the virtual model using the local computing device. During this process, the treating professional selects virtual appliances that embody certain geometric attributes and also selects the positions of the appliances on the patient's teeth within the modeling environment. The modeling software manipulates each bracket and each tooth as a separate object within the 3D environment and fixes the position of each bracket within the 3D space relative to a coordinate system associated with the tooth of the corresponding bracket. The modeling software can then simulate the connection of an archwire with a standard arch form to compute the final positions of the teeth based on the selected positions of the appliances and display the virtual teeth in their final occlusion.

If the treating professional is not entirely satisfied with the final predicted positions of the teeth, the treating professional may use the modeling software to move one or more of the virtual appliances relative to the virtual teeth. The modeling software will then compute and display new final positions of the virtual teeth based on the revised positions of the virtual appliances on the virtual teeth. These steps can be repeated as many times as desired until the treating professional is satisfied with the final positions of the virtual teeth as represented by the modeling software.

As an alternative to positioning appliances, the treating professional may use the modeling software to directly move the virtual teeth to desired positions. In some embodiments, the modeling software will then compute positions of the appliances on the teeth for moving the teeth to those desired positions. Data representing the desired positions of the appliances, along with identification data for each appliance (such as brand name and the manufacturer's part number), tooth identification data (such as tooth type and location in the oral cavity) and patient data (such as name and birth date, or a patient identification number) may then be submitted to a manufacturing facility. This data can then be used by the manufacturing facility to prepare a bonding tray or jig to bond physical appliances to the patient's teeth. Suitable indirect bonding trays and methods for making indirect bonding trays are described, for example, in issued U.S. Pat. No. 7,020,963 (Cleary at al.) and U.S. Pat. No. 7,188,421 (Cleary at al.), U.S. Patent Publication No. 2005/0074717 (Cleary et al.), and pending U.S. Patent Publication Nos. 2006/0223031 (Cinader et al.), and 2006/0223021 (Cinader et al.).

As still another alternative, the computing device at the treating professional's office may include subprograms suitable to analyze the existing malocclusion of the patient and assist in determining the desired ultimate positions of the appliances on the patient's teeth. The software may also include subprograms to assist in suggesting or selecting the proper appliances for treatment of the particular malocclusion at hand. As yet another option, the steps in block 104 may be carried out by a technician at a location remote from the treating professional's office. For example, a technician at a manufacturer's facility may use software to place virtual appliances on the virtual dental model in accordance with known standards in the art or in accordance with general guidelines previously provided by the treating professional.

Once the technician is satisfied with the appliance positions and the resulting finished positions of the teeth, the virtual model together with the data representing the appliance positions is forwarded to the treating professional for review. The treating professional can then either approve the technician's appliance placement positions or reposition the appliances as desired. The treating professional then forwards the virtual model together with the appliance tooth and patient data as mentioned above back to the manufacturer. As before, the desired positions of the teeth (block 104) can then be derived from the selected positions of the appliances in their final occlusion. Some of the above methods are disclosed in further detail in pending U.S. Patent Publication No. 2008/0233531 (Raby et al.).

Treatment and Reduced Image Acquisition

Next, and as indicated in block 106 in FIGS. 1-3, the patient proceeds with orthodontic treatment. In embodiments where brackets and bands are connected to the patient's teeth, an orthodontic archwire can be connected to the bonded appliances to initiate orthodontic treatment. However, alternative forms of orthodontic treatment, such as placement of an aligner tray or functional appliance, may also be used to impart forces to move teeth.

In the Appliance Revision workflow in FIG. 3, a proposed specification of an orthodontic appliance is additionally provided as indicated in block 107. Preferably, this specification characterizes an appliance used during the course of orthodontic treatment in block 106. In some embodiments, this specification includes a set of numerical values defining physical dimensions or other geometric aspects of the orthodontic appliance. For example, the proposed specification (block 107) can include a set of in-and-out, torque, and angulation values for a customized orthodontic archwire that was placed in a patient to initiate treatment in block 106. Depending on the nature of orthodontic treatment used, the proposed specification (block 107) may optionally be directed to other appliances, such as aligner trays, customized orthodontic brackets, or off-the-shelf orthodontic brackets.

In block 108 of FIGS. 1-3, a second digital image representing the second dental arrangement is then provided. Preferably, this step occurs after a suitable period of treatment time has elapsed such that the patient's teeth have assumed a second dental arrangement, where at least one tooth in the second dental arrangement is in a different position than the corresponding tooth in the first dental arrangement. As used, "different position" indicates that the tooth in the second dental arrangement is rotated and/or translated in 3D space with respect to the corresponding tooth in the first dental arrangement (i.e. the term "position" relates both angular orientation and location in x, y, z coordinate space).

The second digital image may be provided by re-scanning the patient using 2D or 3D X-rays, MRI, or laser light scanning techniques and processing the digital data as described previously. As an alternative, the raw data may be provided by scanning a positive or negative physical dental model representing the second dental arrangement.

Preferably, and as indicated in block 108, the digital image representing the second tooth arrangement is a reduced image compared with the first digital image in block 100. As used herein, when comparing two images of a given object, one image is referred to as a "reduced image" when it includes less data, or fewer details, than the other image. Conversely, the other image is referred to as a "supplemented image" on the basis that it contains additional data or details about the object not present in the "reduced image". Use of reduced images can be advantageous because less memory is needed to store these images and less computing power is required to process and manipulate them. Even more significantly, less time is typically required to acquire reduced images, resulting in significant time savings at an orthodontic office or scanning facility. In more detail, reduced images can be advantageously provided as shown in FIGS. 4-6 and the description that follows.

Figure 4:
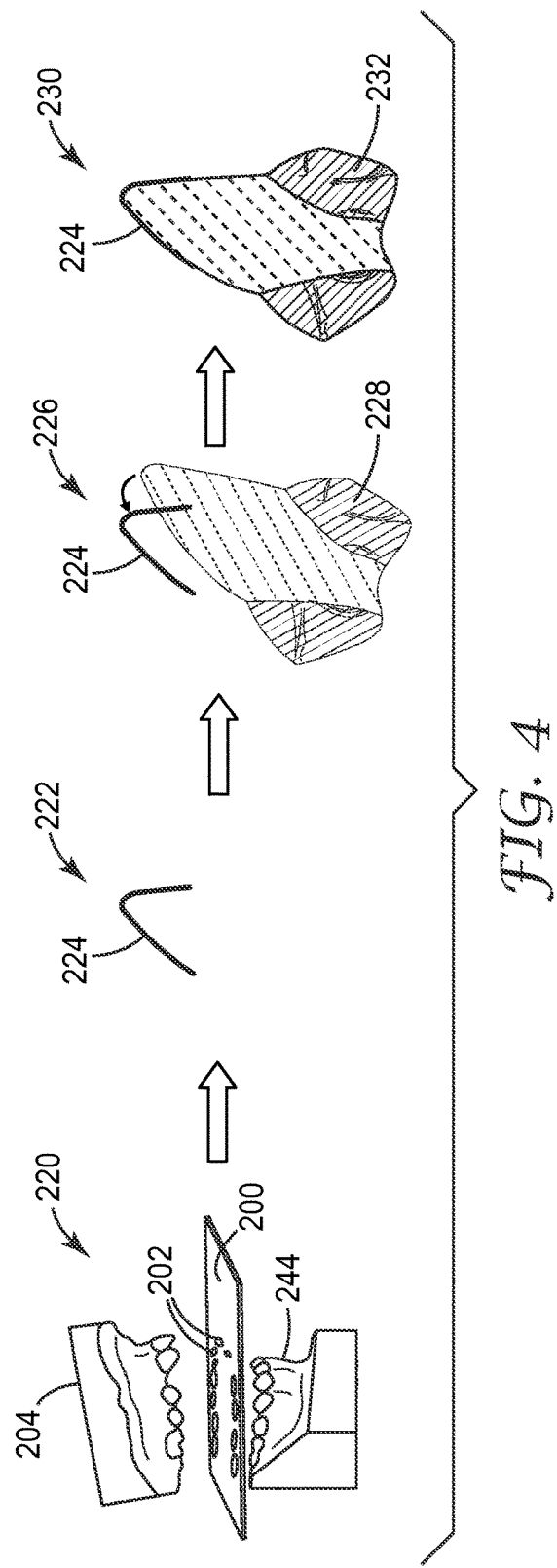
FIG. 4 shows the imprint of a patient's dentition represented by the surface of a bite register in FIG. 7.

FIG. 4 in step 220 shows one exemplary embodiment in which just the occlusal surfaces of teeth are provided using a bite plate 200. Bite plate 200 is a simple block of malleable material that records the shape, location, and orientation of some or all of the teeth in a current dental arrangement 244 of the lower arch when the jaws are clenched on the bite plate 200. Preferably and as shown, the bite plate 200 acquires impressions of the upper and lower jaws simultaneously, which advantageously relates both tooth positions within one jaw and tooth positions between jaws. Malleable materials that may be used for bite plate 200 include wax, alginate, polyvinyl siloxane, acrylic, plastic, plaster or any other suitable impression material that does not distort upon disengagement from the teeth. The bite plate 200 is shown here with a generally rectangular configuration, but may also have a generally "U"-shaped configuration to conserve material. Any other reasonably flat slab of malleable material that extends across the occlusal surfaces of the teeth may also be used. After the impression is taken, imprints 202 are formed on bite plate 200 to provide a three-dimensional representation of at least a portion of the current dental arrangement 244. If desired, two or more bite plates 200 may be used to capture all of the teeth of interest in current dental arrangement 244. Using a bite plate 200 is particularly convenient when appliances are connected to the teeth, since the appliances and the bite plate 200 do not interfere with each other.

As shown in step 222, a second digital image 224 is then provided by scanning the bite plate 200. This may be accomplished using a scanner with active wavefront sampling, laser light scanning, contact probes, or any of the other methods described earlier. Optionally, the raw data is cleansed, surfaced, and/or otherwise processed prior to generating the image 224. In cases where multiple bite plates 200 were used, there may be multiple images 224. The multiple images 224 can later be registered and recombined with each other in software. The scanning of the bite plate 200 may take place immediately at the orthodontic office, or alternatively the bite plate 200 may be scanned at an off-site location if a scanner is not available. Because the second digital image 224 in this embodiment represents only the occlusal tooth surfaces of the current dental arrangement 244, it is a reduced image compared with the first digital image provided in block 100.

Figure 5:
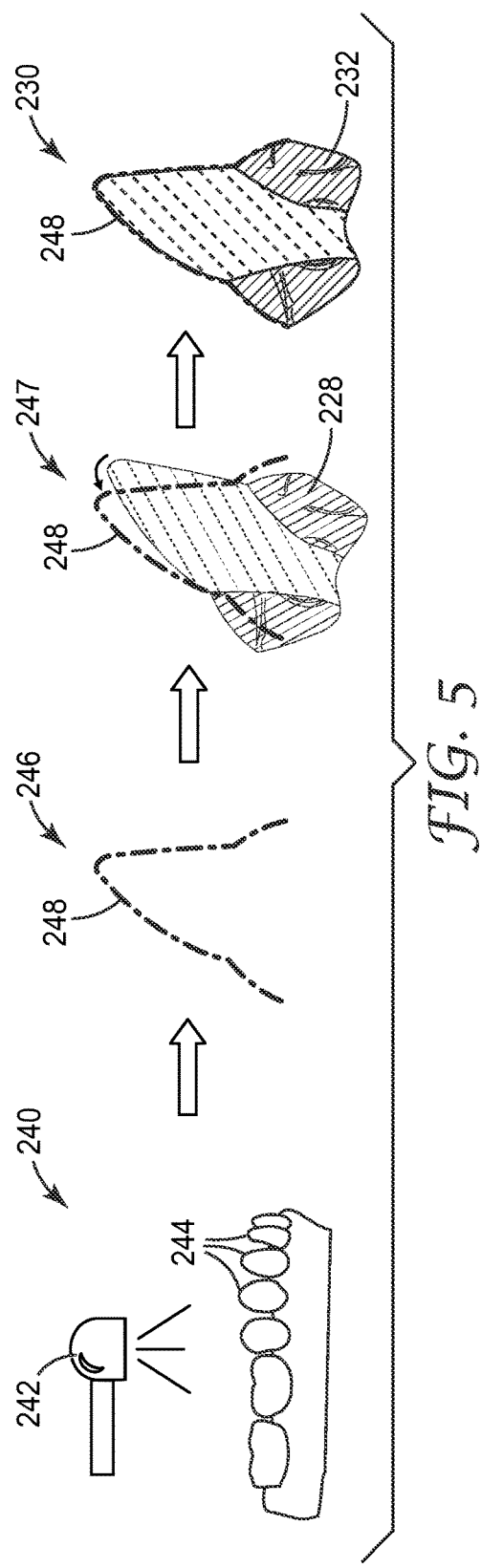
FIG. 5 shows a workflow showing the process of registering a tooth element within a dental arrangement using a bite register.
Figure 6:
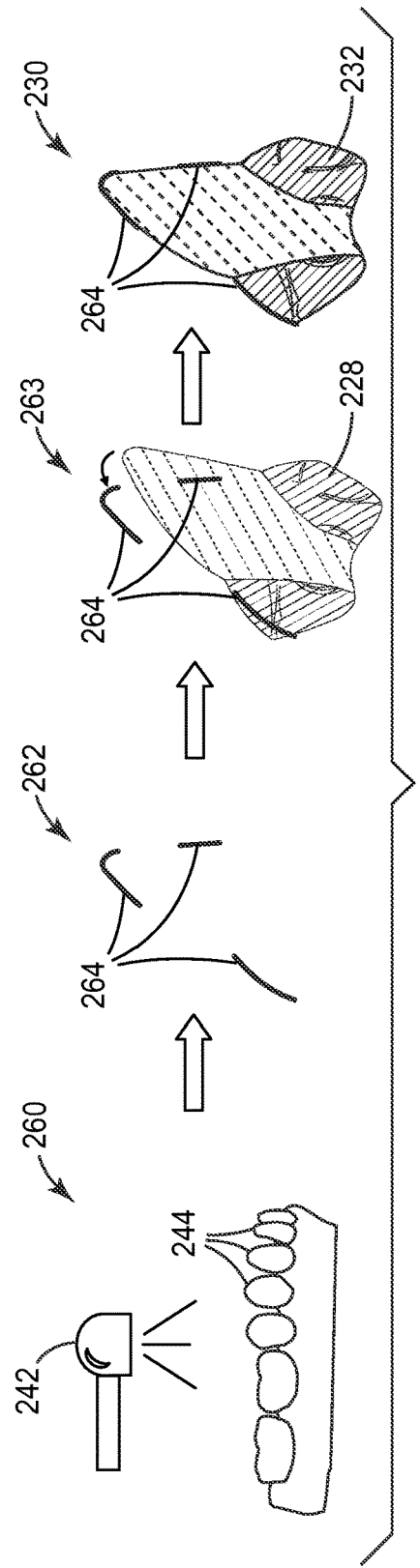
FIG. 6 shows a workflow showing the process of registering a tooth element within a dental arrangement using a low resolution intraoral scan.

For the sake of simplicity in this illustration and subsequent illustrations to be discussed in FIGS. 5 and 6, the second digital image 224 shows only a single element in cross-section representing a single tooth of the current dental arrangement 244. However, it is envisioned that the second digital image 224 may contain two or more elements representing two or more respective teeth. In some embodiments, the second digital image 224 includes at least three independently movable elements representing at least three respective teeth in the current dental arrangement 244. It is especially advantageous if second digital image 224 includes elements corresponding to each tooth in the upper and lower jaws, along with at least one element pertaining to a TAD or dental feature that does not move during treatment. By capturing both dental features that are both movable relative to the jawbone (e.g. teeth) as well as immovable relative to the jawbone (e.g. TADs), it is possible to register elements of multiple second digital images 224 taken at different times during treatment under a single unified coordinate system. This in turn enables a treating professional to superimpose images of dental arrangements and quantify tooth movements, as will be discussed later.

In a second embodiment depicted in steps 240 and 246 of FIG. 5, a reduction in the resolution of the intraoral scan may be used to provide a reduced image. Suppose that the first digital image provided in block 100 was acquired using an intraoral scanner operating at a first resolution. In step 240, a handheld scanner 242 operating at a second resolution lower than the first resolution may then scan the surfaces of some or all of the teeth in the current dental arrangement 244. The scan data is optionally cleansed and processed and then used to derive a second digital image 248 exhibiting a lower point density than that of the first digital image provided in block 100. By virtue of the reduced point density, scanned surfaces in the second digital image 248 are lacking in detail (e.g. having a reduced number of triangles in the 3D mesh representation) compared with corresponding scanned surfaces in the first digital image in block 100. As such, the second digital image 248 is a reduced image compared to the first digital image provided in block 100.

The second digital image 248 may represent the same portions of the dentition represented by the first digital image in block 100 or, alternatively, may provide a subset or a superset thereof. That is, the overall area of the intraoral cavity that is scanned to produce the second digital image 248 may include areas greater or lesser than that included in the first digital image (block 100). For clarity, elements of interest in the second digital image 248 may be digitally "cropped" from other elements of the scanned image such as the gingiva and surrounding tissue. As before, the current dental arrangement 244 may include the upper jaw, lower jaw, or both simultaneously. Optionally, the scanner 242 may scan the jaws first in an open position to image occlusal and lingual teeth surfaces and then scan again in a closed position to relate the positions of the upper and lower teeth with each other. TADs may also be included in the current dental arrangement 244. If TADs are included, scanner 242 may additionally scan the head portions of any TADs such that the second digital image 248 relates the TAD positions to those of adjacent teeth.

There are other advantages to using a low resolution scan to provide the second digital image 248. A major advantage is that a low resolution scan can be completed more quickly than a full or high resolution scan of the same surface area for a given dental arrangement. This advantage in speed translates to shorter chair time for the doctor and staff and increased comfort to the patient. Increasing scan speed may be particularly beneficial if intraoral scans are routinely conducted at each orthodontic appointment, since the cumulative reductions in chair time throughout the course of a day may allow an orthodontic office to see more patients. Secondly, scanning at a lower resolution relaxes the demands on the memory, system resources to process the data, and ultimately, hardware required to complete an intraoral scan within a short amount of time. A low resolution scanner is also likely to be more cost effective than a high resolution scanner for many orthodontic offices. For example, an initial scan may be conducted using a high resolution scanner at an off-site location, and routine intraoral scans conducted thereafter using a less expensive low resolution scanner at the orthodontic office.

In a third embodiment and as shown in steps 260 and 262 of FIG. 6, a partial intraoral scan may be used to generate 3D data used to produce a reduced image. Similar to the bite plate 200, a partial intraoral scan provides a reduced image by virtue of capturing only parts of teeth in the current dental arrangement 244. However, the partial intraoral scan is not limited to the occlusal surfaces of the teeth. A partial scan may additionally include lingual or facial surfaces of the teeth, or a combination or sub-combination of occlusal, lingual, and facial surfaces. Optionally and as shown in step 262, the partial intraoral scan can generate a second digital image 264 that includes a combination of partial lingual, facial and occlusal surfaces.

Preferably the scanned surface area in step 260 is small compared with the overall surface area of the current dental arrangement 244. Since the operator of the intraoral scanner need only capture key landmarks for each feature of interest in the current dental arrangement 244, the time spent scanning is significantly reduced. In some embodiments, the partial scan is conducted by only scanning the occlusal surfaces of the teeth, which tend to be topologically distinct and are conveniently accessible by a handheld scanner. Preferably, the scan data includes the occlusal surfaces of every tooth in the arch, and is sufficient (e.g. including at least three points in 3D space) to allow independent registration of each tooth element. As already shown, shortening the time to conduct an intraoral scan or alleviating difficulties in conducting an intraoral scan increases efficiency and would be welcome by both the treating professional and patient.

During conventional orthodontic treatment, it is common for the current dental arrangement 244 to include appliances connected to the teeth. If the initial digital image in block 100 also includes these appliances, then scanning these appliances in steps 240,260 can be highly advantageous for registration purposes. This is the case because most bonded appliances, such as brackets, have a very well defined 3D structure or geometry. As such, these structures are well suited to provide landmarks for registering elements from the first digital image in block 100 to corresponding elements in images provided later in treatment. Scanning a bonded appliance that has a well-defined geometry may also assist in automating the definition and registration of landmarks. In a fully bonded case, it is even contemplated that merely scanning the appliances rather than scanning all of the tooth surfaces can be sufficient for registration. This is possible since the location and orientation of each appliance is fixed relative to a respective tooth in current dental arrangement 244.

As an additional option, the current dental arrangement 244 may include the exposed head portions of at least one TAD implanted in the patient's jawbone. Including TADs in the intraoral scans 240,260 offers further unique advantages that shall be examined in the next section.

Registration

In the Treatment Monitoring and Treatment Evaluation workflows depicted in FIGS. 1-2, respectively, the process of registration occurs in block 110. Registration is often described as the alignment of two objects such that features of one object map (or coincide or align) on top of corresponding features of the other object. While physical registration can take place between actual objects, the examples described herein describe virtual registration, which takes place between digital images on a computing device.

As indicated by block 110, elements of the first digital image (block 100) are registered to corresponding elements of the second digital image 224,248,264 (block 108). The registration process is further illustrated, in an exemplary cross-sectional view, for a single tooth element in each of FIGS. 4-6. Step 226 of FIG. 4 shows the first digital image 228, which includes a tooth crown, tooth root, and a small portion of the surrounding gingiva, being rotated counter-clockwise to register to the second digital image 224. In similar fashion, step 247 of FIG. 5 shows the first digital image 228 being registered with second digital image 224, and step 263 of FIG. 6 shows the first digital image 228 being registered with the second digital image 264. As shown in each of these examples, only a small portion of the total amount of data is needed to allow for a precise registration between the transformed first digital image 228 and the second digital image 224,248,264. The amount of detail provided in digital image 228 can vary. For example, the digital image 228 may show just the tooth element itself without the surrounding gingiva or alternatively just a portion of the tooth element, such as the crown.

Obviously, the registration between first digital image 228 and second digital image 224,248,264 is not limited to a single tooth element. If the images to be registered include multiple elements representing multiple teeth and/or appliances, corresponding elements are paired and the process is repeated for each pair until all dental features of interest are registered in a common coordinate system. In some cases, size discrepancies exist between image 228 and image 224,248,264 because different scanning methods were used to provide the digital images. If size discrepancies do exist, it may be further necessary to scale one or both images beforehand so they can be properly registered with each other.

The Appliance Revision workflow in FIG. 3 differs slightly from the Treatment Monitoring and Treatment Evaluation workflows in two respects. First, the registration step provided in block 111 takes place between the image of teeth in desired positions in block 104 (i.e. target digital image) and the second digital image 224,248,264. Although the image of desired teeth positions (block 104) is not explicitly provided in FIGS. 4-6, the registration process in block 111 is essentially the same as that previously shown between the first digital image 228 and the second digital image 224,248,264. As before, the image of teeth in desired positions (block 104) is preferably a supplemented image compared to the second digital image 224,248,264.

Second, the treating professional has the option of bypassing the registration step in block 111 altogether if the teeth have already arrived at the desired positions. As indicated in block 112, the dental arrangement according to the second digital image 224,248,264 is first compared with the target dental arrangement derived in block 104. If these two digital images match within a pre-determined tolerance, then no registration step is needed and the workflow proceeds to the next phase of treatment in block 114. On the other hand, if the digital images do not match, the process continues to block 111, where the elements of the image of teeth in desired positions are registered with elements in the second digital image 224,248,264, as discussed earlier.

The registration steps in blocks 110,111 can be facilitated by the use of landmarks. A landmark is a common point, series of points, or surface that is easily identified and can be used to register digital images with each other. By reducing the amount of digital data that is compared, landmarking can simplify and speed the process of registration. At least three common points in space are generally used to register two 3D objects; however, increasing the number of points and distances between points can further improve accuracy. Landmarks may be used to register digital images within a single dental arrangement, or between two or more dental arrangements at different stages of treatment. In some embodiments, landmarks are generated manually. For example, a user may use an input device such as a mouse to select locations on a tooth to define a desired landmark.

Also, as mentioned previously, the orthodontic appliances themselves (or other objects connected to the teeth) may be used to define landmarks. For example, if an intraoral scan is performed on teeth with bonded appliances, a user can view the digital images 228,248,264 on a display and select mesial, distal, occlusal, and gingival bracket surfaces for use as landmarks. In this instance, using bracket edges, corners, or surfaces as landmarks can be advantageous because these bracket features often have sharp and well defined boundaries. In some embodiments, this process is also used to identify landmarks on the second digital image. If desired, landmarks may be based on earlier user input or generated automatically or semi-automatically. For example, a computing device using an image analysis method may define landmarks using cusp locations on the occlusal crown surfaces of each tooth. Alternatively, if the appliances have known geometries, then a computing device may be used to automatically identify the appliances in the images 248,264, 228, and define landmarks on the same. Other types of landmarks are possible, such as those derived from user applied markers, as described in published U.S. Patent Publication No. 2007/0141525 (Cinader et al.).

Once landmarks have been established, registration occurs by virtually orienting the first digital image in block 100 relative to the second digital image 224,248,264 such that corresponding landmarks between the transformed first digital image 228 and the second digital image 224,248,264 coincide. The process can be executed using, for example, the "Compare" or "Best-fit alignment" function in the commercial software package Geomagic Qualify (available from Geomagic Inc.). Registration takes place by aligning selected surfaces of the first digital image 228 to the second digital image 224,248,264. The registration is complete when the computing device determines the best-fit position within a predetermined tolerance.

Registration may be fully automated or semi-automated in that user verification or other input may be requested. In some embodiments, the computing device may search the surface data of the transformed first digital image 228 for at least one pre-defined landmark, where the landmark is defined to be on a tooth surface or appliance in the first dental arrangement in block 100. In alternative embodiments, the computing device may search the surface data of the second digital image 224,248,264 for at least one corresponding pre-defined landmark, where the landmark is defined to be on a tooth surface or appliance in the current dental arrangement 244. Once the first digital image 228 has been registered with the second digital image 224,248,264, the computing device optionally records the mathematical transformation to register the coordinate system of image 228 with the coordinate system of image 224,248,264. This information can be used to describe the extent of tooth movement that occurred during treatment.

Along with tooth structures and bonded appliances, the registration of image elements in steps 226,247,263 can also include structures that do not move relative to the jawbone during treatment. In some embodiments, these structures include oral structures such as frenum (folds of mucous membrane and underlying tissue), rugae (irregular ridges located on the palate) or implanted devices such as TADs. With implanted devices, it can be particularly beneficial to combine a reduced image provided by an intraoral scan with a supplemented image that provides information including embedded portions of the device. For example, an image of the 3D head structure of a TAD may be provided by scanning a patient at a routine office visit and subsequently registered with a full 3D image showing both the head and embedded tail portions of the TAD. The full 3D image showing both the head and tail of the TAD may be known in advance and provided by the TAD manufacturer, scanning the device prior to installation, or scanning the patient using a technique such as X-ray radiography, CT scanning, MRI, or ultrasound imaging any time after installation. Since the head geometry of the TAD is known beforehand, it can be also be inputted into the computing device and used to define a landmark associated with this device automatically.

Including TADs in the first digital image 228 is particularly beneficial for registering images that include multiple elements. Since TADs do not move (or move minimally) during treatment, these devices can provide fixed landmarks that are referenced to the jawbone. These fixed landmarks in turn facilitate the superposition of an image of a first dental arrangement taken at a first time during treatment with an image of a second dental arrangement taken at a second time during treatment. Moreover, as with brackets and other orthodontic appliances, TADs are advantageous in that they have precisely defined geometries that facilitate registration of images with each other (blocks 110,111). In a preferred embodiment, the first digital image 228 includes both tooth elements as well as TAD elements. Then, after the second digital image 248,264 is provided using a scanner, these elements are registered with corresponding elements in the image 248,264 to produce a composite image showing the positions of one or more implanted TADs relative to the roots of the teeth.

Application

Depending on the specific needs of the treating professional, the information provided in the registration process can enable different aspects of orthodontic treatment planning. By quantifying the movement of teeth in a way that is both precise and objective, these methods can assist a treating professional in simulating tooth movement, developing a treatment plan, and even configuring appliances. The Treatment Monitoring, Treatment Evaluation, and Appliance Revision workflows each provide particular applications and advantages, and these are discussed in greater detail below.

In the Treatment Monitoring workflow shown in FIG. 1, the transformed version of first digital image 228 is used to derive a digital image (block 116) that can be viewed by a treating professional. In further detail, this is illustrated by the final step 230 in each of FIGS. 4-6, which shows the derivation of a third digital image 232 based on the transformed first digital image 228. The third digital image 232 is used, in turn, to produce a viewable digital image that can optionally be scaled, rotated, and manipulated by a user on a display. As shown, the third digital image 232 includes crown and root portions of the tooth and portions of surrounding gingiva in cross-section, as might be provided by X-ray radiography, a CT scan, MRI, or ultrasound imaging. The third digital image 232 is therefore a supplemented digital image compared to each of the second digital images 224,248,264. If desired, this process may be repeated throughout treatment at regular intervals to provide a series of images that chart movement of this tooth over time.

It is worth noting that the third digital image 232 advantageously has a level of completeness and detail limited only by that of the first digital image 228, and not limited by the second digital image 224,248,264. The third digital image 232 can be used for diagnostic, treatment planning, and other applications as seen fit by the treating professional. Here, it is shown here for a single tooth, but each dental structure in the current dental arrangement 244, including TADs if present, may be similarly registered and re-constructed as long as the dental structure maintains a reasonably uniform shape during treatment. In a preferred embodiment, the third digital image 232 includes each tooth element in the current dental arrangement 244 and reveals both the visible crown portions of the teeth as well as hidden surfaces of the teeth roots integrated into a single 3D model. The third digital image 232 can then be shown on a display, and may be scaled and rotated to observe the relative positions of teeth. Other diagnostic tools, such as point-to-point measurements and cross-sectioning, can also be implemented.

In the Treatment Evaluation workflow in FIG. 2, the actual teeth positions are juxtaposed with the desired teeth positions for comparison by a user such as a treating professional. For example, block 118 shows the third digital image 232 representing actual tooth positions superimposed on the image from block 104 representing desired tooth positions. The same principles used to register individual elements with each other can likewise be used to register composite images with each other. As mentioned earlier, landmarks defined by TADs, rugae or other dental features that do not move during treatment are preferably used to register the third digital image 232 and the image in block 104. These 3D images can then be superimposed on a display using commercially available software, such as Geomagic Qualify. As alternatives to superimposing the images, a user may instead display the images side-to-side, or toggle between images of teeth positions to visualize the movement of teeth between the first and second dental arrangement.

At this point, the process continues to block 120, where the two images are compared with each other to determine if there is an acceptable match. This step may be carried out by a treating professional, in which case a human may rotate and manipulate the superimposed 3D images and subjectively determine if the desired tooth positions in block 104 have been achieved. In other embodiments, a computing device may automatically make this determination under the appropriate supervision of a treating professional. For example, the decision may be based on matching within certain absolute or relative tolerance limits around the desired tooth positions. If an acceptable match is achieved, then the process continues to the next phase of treatment according to block 114. At this point, the treating professional may choose to end active treatment, define a new treatment goal and restart the process from block 104 by deriving a new set of desired tooth positions, or start an entirely different workflow altogether. If an acceptable match is not achieved, then the process proceeds to block 121, where the treating professional has the option of making adjustments to at least one orthodontic appliance in order to bring the dental arrangement into conformance with the desired tooth positions in block 104. If and when these adjustments are made, orthodontic treatment continues as indicated by block 106 and the process starts over.

In instances where orthodontic treatment involves TADs or other implanted appliances, this workflow provides additional advantages. As discussed earlier, complete 3D images of TADs including the embedded tail portions can be acquired at the beginning of treatment using, for example, a CT scan in block 100 and then registered with reduced images of the same TADs provided by an intraoral scan 240,260 during the course of treatment. The third digital image 232 is therefore a composite image that shows not only the head portions of the TADs but also the embedded tail portions of the TADs alongside the tooth roots. This is beneficial to the patient since additional X-rays or CT scans are not needed beyond the initial scan at the beginning of treatment and radiation exposure is kept to a minimum. This method is also highly beneficial to the treating professional since it effectively tracks the movement of teeth relative to the TADs over time. By tracking tooth movement in regular intervals throughout treatment, it is also possible to simulate the movement of teeth and anticipate collisions between TADs and teeth before they actually occur.

In some embodiments, the Treatment Evaluation workflow further includes measuring differences in corresponding tooth positions between the target dental arrangement and the second dental arrangement to provide a treatment index. Once the image of actual teeth positions has been derived (block 118), this treatment index can be determined based on the translational and rotational deviations between images of the actual teeth positions and the desired teeth positions (block 104). More particularly, the treatment index may be calculated by pairing corresponding tooth elements between the two images and measuring the translational and rotational deviations for each pair. Optionally, the treatment index may be provided for each tooth, or provided as an average across all teeth or fewer than all of the teeth. Alternatively, the treatment index may be expressed as a percentage showing the extent of progress in moving teeth from initial positions to desired positions. As an example, the deviations between actual teeth positions (block 118) and desired teeth positions (block 104) may be calculated, and divided by the deviations between initial teeth positions (block 100) and desired teeth positions (block 104).

In the Appliance Revision workflow, the registration process (block 111) is similarly used to revise the specification to the orthodontic appliance proposed in block 107. Block 122 shows the derivation of a revision by recording the transformation matrix used to register elements of target digital image (block 104) to corresponding elements in the second digital image (block 108). The process of block 122 is then repeated for each element of interest in the second digital image, typically for each individual tooth in the current dental arrangement 244. The transformation matrix, or set of transformation matrices, is then wholly or partially used to derive a revision to the proposed specification from block 107. Since each transformation matrix fully describes the translational and rotational deviations between the desired and actual tooth positions, this data can derive precise modifications to the in-and-out, torque, and angulation values in the specification of an orthodontic appliance.

In some embodiments, the revised specification is used to produce a new custom bent orthodontic archwire such as provided by Orametrix, Inc. (Dallas, Tex.), or a new removable appliance such as a polymer aligner shell manufactured by Align Technology, Inc. (Santa Clara, Calif.). In other embodiments, the specification is used to produce other customized fixed or removable appliances such as orthodontic brackets, springs, correctors, or functional appliances. In still other embodiments, the specification may instead assist the treating professional in selecting off-the-shelf appliances, such as brackets. Depending on the type of appliance used, it is also possible for the specification to incorporate other aspects of treatment; for example, the torque specification may include a factor of "overcorrection" to overcome torque loss in the archwire slot of an orthodontic bracket. In still other embodiments, the specification is used to adjust the position of the appliance relative to the teeth rather than modify the structure of orthodontic appliance. For example, the act of revising the orthodontic appliance may be carried out by configuring a device, such as a bonding tray or jig, which locates the appliance relative to a dental structure such as a tooth to express the proposed specification.

The process then continues with block 124, in which the treating professional decides whether or not to accept the suggested appliance revision. If the revision is accepted, then the revision takes place as shown in block 126. Following the installation of the revised appliance, orthodontic treatment then resumes, as indicated by block 106. Conversely, if the treating professional decides not to accept the appliance revision, then orthodontic treatment also resumes according to block 106, except without changes to the current orthodontic appliance.

It should be understood that the methods described in these workflows are presented as examples only and are not mutually exclusive of each other. Aspects of the Treatment Monitoring workflow may be included in the Appliance Revision workflow and vice versa. Similarly, aspects of the Treatment Evaluation workflow may be incorporated into the Appliance Revision workflow and vice versa. For example, the Appliance Revision workflow could optionally be expanded to include steps to derive and display a third digital image showing the patient's current dentition (blocks 110 and 116), even though these steps are not explicitly provided for in FIG. 3.

A software program stored on any conventional medium could be programmed to execute any of the methods described above. In some embodiments, the software program includes a rendering engine that accesses and renders 3D digital data to generate the 3D images described in the above methods. The software program may further include a registration module that automatically registers digital images with each other. By generating 3D digital images and registering the images with each other, respectively, the rendering engine and registration module facilitate each of the Treatment Monitoring, Treatment Evaluation, and Appliance Revision workflows described above.

The software program may be installed on a DVD, flash memory, or hard drive in a back office server or workstation at an orthodontic office, a server at a manufacturing facility, or combination thereof. If desired, the software may also be accessed remotely through the Internet. Further, the software may also be installed at a facility where X-ray radiography, laser scanning, CT scanning, MRI, or ultrasound imaging is conducted. It is also envisioned that the software may be located at offices of related specialties, such as periodontal offices, family dental offices, and offices of oral surgeons so that aspects of treatment planning and monitoring may be shared amongst multiple users. For example, an oral surgeon may use the software during the course of a patient's treatment to ascertain the positions of tooth roots prior to the installation of a dental implant or TAD. As demonstrated, using a bite impression 220, low resolution scan 240, or partial scan 260 is advantageous because a given office can quickly and efficiently generate a comprehensive 3D dental model upon a patient's arrival that can be shared with other dental professionals.

EXAMPLE

Aspects of the methods above are further demonstrated by the following example. A physical dental model of the upper and lower jaws, made from orthodontic stone, was provided by a local orthodontic office. For exemplary purposes, this dental model was used to simulate a patient's dental structure in a given dental arrangement. To prepare the first digital image, a polyvinylsiloxane impression was first taken using POSITION PENTAQUICK brand impression material available from 3M ESPE (St. Paul, Minn.). After allowing the impression to set for 90 seconds, it was removed from the dental model and used to cast a duplicate positive model from F82-302 epoxy resin from United Resin Corporation (Royal Oak, Mich.). To impart opacity to the epoxy model, it was coated with a fine layer of SPOTCHECK brand SKD-S2 Developer white talc powder from Magnaflux (Genview, Ill.). The coated model was then scanned using a SURVEYOR brand OM-3R narrow spectrum visible light laser scanner from Laser Design, Inc. (Bloomington, Minn.). The raw point cloud data provided by the scanner was then surfaced using Geomagic Studio to generate 3D surfaces of the teeth along with the surrounding gingiva. The Geomagic Dental Module, also provided by Geomagic, Inc., was finally used to virtually separate the tooth surfaces and gingival surfaces from each other to produce individual, movable tooth elements. These 3D tooth elements represent supplemented images that shall be used in the registration process.

Figure 7:
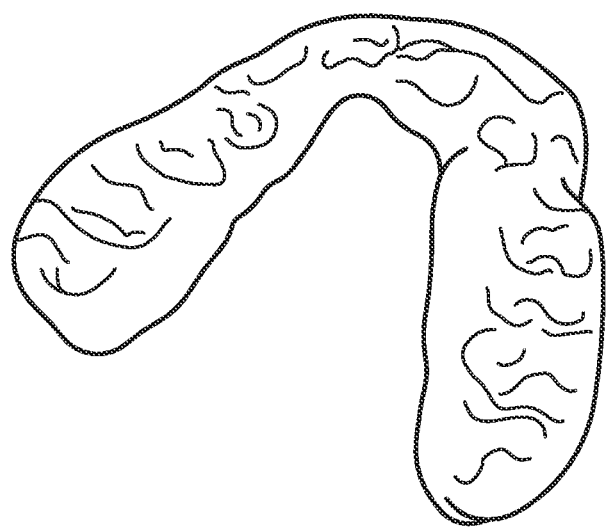
FIG. 7 shows a screenshot of the virtual bite plate, revealing the occlusal surfaces of teeth on the upper dental arch.

In order to prepare the reduced image, a bite plate made from EXPRESS BITE brand polyvinylsiloxane from 3M ESPE (St. Paul, Minn.) was placed between the upper and lower jaws of the original stone dental model. The jaws were then firmly pressed together to imprint the occlusal surfaces of the upper and lower teeth on the bite plate. The bite plate was then scanned using the OM-3R narrow spectrum visible light laser scanner to produce digital image data that was processed as before to surfaces identical to the physical bite plate. FIG. 7 illustrates the virtual bite plate, revealing the occlusal surfaces of teeth on the lower dental arch. The bite plate image and the separated 3D tooth images were then imported into Geomagic Qualify.

Figure 8:
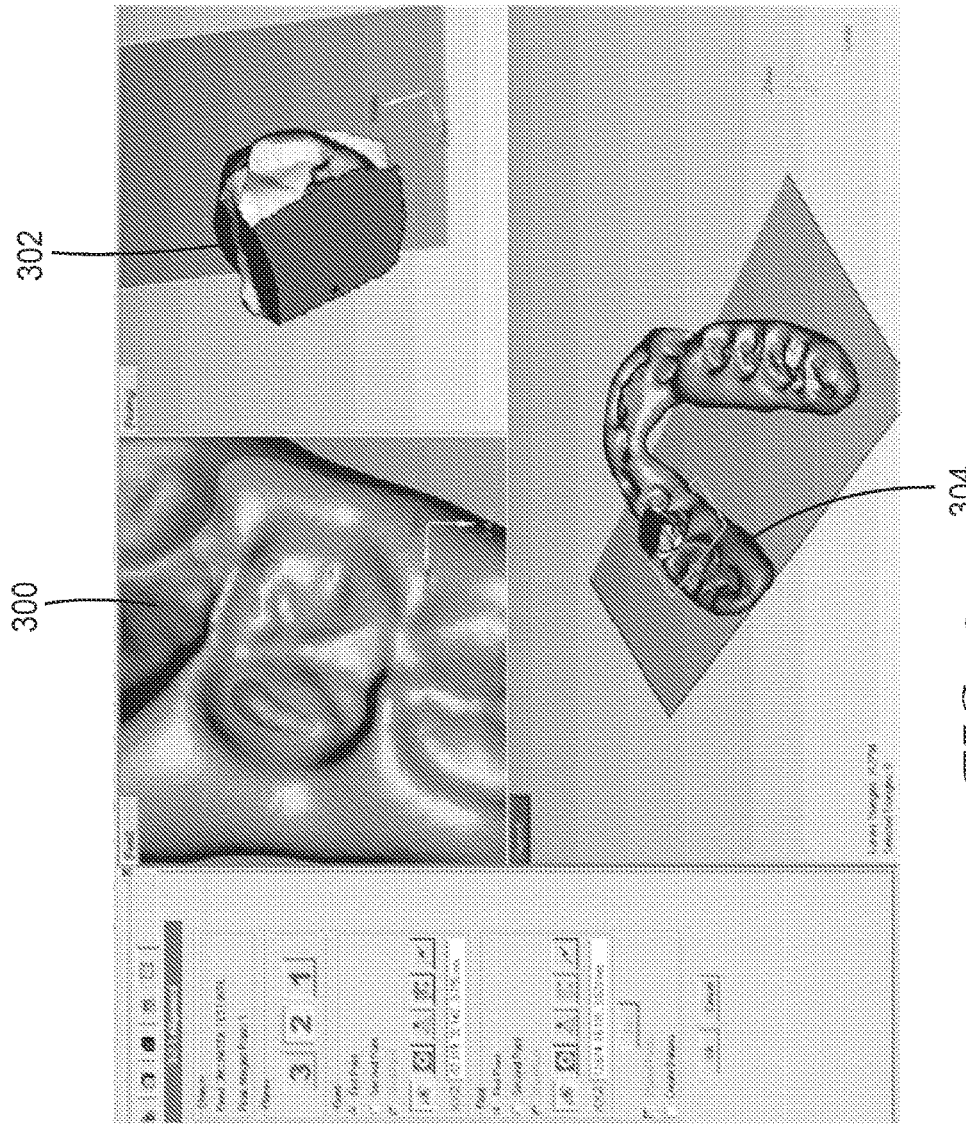
FIG. 8 shows a screenshot demonstrating the registration process using the virtual bite plate in FIG. 7.

FIG. 8 shows a screenshot demonstrating the registration process. The virtual bite plate image has been selected as the fixed reference image, and is shown in window panel 300. In this example, the digital image corresponding to the upper left second bicuspid tooth was defined as the floating image and is shown in window panel 302. Using the 3-2-1 Alignment feature of Geomagic Qualify, the digital tooth image was then registered with the bite plate impression image using a best-fit algorithm such that their respective occlusal surfaces were exactly superimposed on each other. The final positions of the two images are shown in window panel 304. Although not shown here, other teeth may be registered in a similar fashion. This example demonstrates the registration of an image showing the entire crown of the lower left second bicuspid tooth using only a bite plate impression. Successive iterations of this process may then be performed in order to reconstruct the remainder of the dental arrangement based on the occlusal surfaces shown in window panel 304.

The foregoing invention has been described in some detail by way of illustration and example for purposes of clarity and understanding. However, various alternatives, modifications, and equivalents may be used and the above description should not be taken as limiting in the scope of the invention which is defined by the following claims and their equivalents.

The invention claimed is:

1. A computer-implemented method of deriving an image of a dental arrangement of a patient useful in manufacturing an orthodontic appliance, the method comprising the steps of performed by a computing device:
    storing into a memory of the computing device a first digital image representing a first dental arrangement of the patient at a first time, wherein the first digital image is provided by intraorally scanning the first dental arrangement at a first resolution;
    storing into the memory a second digital image representing a second dental arrangement of the patient at a second time after some actual orthodontic treatment has elapsed following the first time, wherein the second digital image is a reduced image when compared to the first digital image, wherein at least one tooth in the second dental arrangement is in a different relative position within the second dental arrangement than the corresponding tooth in the first dental arrangement, and wherein the second digital image is provided by intraorally scanning the second dental arrangement at a second resolution lower than the first resolution;
    computing a third digital image representing the second dental arrangement by registering at least one element of the first digital image with at least one corresponding element of the second digital image, wherein the third digital image is a supplemented image when compared to the second digital image, and wherein the third digital image is a three dimensional image that shows the different relative positions of the at least one tooth after the some orthodontic treatment and allows a user to visualize movement of teeth between the first and second dental arrangements;
    comparing the first and second digital images to automatically determine if the first digital image matches the second digital image within an absolute or relative tolerance limits around a desired position of the tooth; and
    if the first and second digital images do not match, then receiving adjustments to the orthodontic appliance to bring the movement of the teeth into conformance with the desired position of the tooth.

2. The method of claim 1, wherein the at least one element of the first digital image includes an element that represents a tooth.

3. The method of claim 1, wherein the at least one element of the first digital image includes at least three elements representing at least three respective teeth.

4. The method of claim 1, wherein the at least one element of the first digital image includes an element that represents an appliance.

5. The method of claim 4, wherein the appliance includes a bonded appliance.

6. The method of claim 4, wherein the appliance is a temporary anchorage device.

7. The method of claim 1, wherein the second dental arrangement includes both the upper and lower arches.

8. The method of claim 1, wherein the step of providing the first digital image occurs prior to the application of orthodontic appliances.

9. The method of claim 8, wherein the second digital image is provided during the course of treatment.

10. A computer-implemented method of comparing dental arrangements of a patient to create an orthodontic appliance, the method comprising the steps of performed by a computing device:
    storing into a memory of the computing device a first digital image representing a first dental arrangement of the patient at a first time;
    computing a target digital image representing a target dental arrangement, the target arrangement representing desired positions of one or more teeth in the first dental arrangement;
    storing into the memory a second digital image representing a second dental arrangement of the patient at a second time after some actual orthodontic treatment has elapsed following the first time, wherein the second digital image is a reduced image compared to the first digital image and wherein at least one tooth in the second dental arrangement is in a different relative position within the second arrangement than the corresponding tooth in the first dental arrangement;

computing a third digital image representing the second dental arrangement by registering at least one element of the first digital image with at least one corresponding element of the second digital image, wherein the third digital image is a supplemented image when compared to the second digital image;

comparing the third digital image to the target digital image to automatically determine if the first digital image matches the second digital image within an absolute or relative tolerance limits around a desired position of the tooth, wherein the third digital image shows the different relative positions of the one or more teeth after the some orthodontic treatment and allows a user to visualize movement of teeth between the first and second dental arrangements; and if the third and target digital images do not match, then receiving adjustments to the orthodontic appliance to bring the movement of the teeth into conformance with the desired position of the tooth, the method further comprising:

storing into the memory a proposed specification of the orthodontic appliance;

registering at least one element of the target digital image to at least one corresponding element of the second digital image to derive a transformation matrix;

revising the proposed specification of the orthodontic appliance based in part on the transformation matrix; and creating the orthodontic appliance based at least in part on the proposed specification.

11. The method of claim 10, further comprising the step of displaying the third digital image superimposed on the target digital image.

12. The method of claim 10, wherein the step of deriving the target digital image includes virtually moving teeth in the first dental arrangement to desired positions.

13. The method of claim 10, wherein the at least one element of the first digital image includes an element that represents a tooth.

14. The method of claim 10, wherein the at least one element of the first digital image includes an element that represents a temporary anchorage device.

15. The method of claim 10, further comprising the step of measuring differences in corresponding tooth positions between the target dental arrangement and the second dental arrangement to provide a treatment index.

16. The method of claim 10, wherein the orthodontic appliance is an archwire.

17. The method of claim 10, wherein the orthodontic appliance is a removable appliance.

18. The method of claim 10, wherein the orthodontic appliance is a fixed appliance.

19. The method of claim 10, wherein the step of revising the orthodontic appliance is carried out by configuring a device that locates the appliance relative to a dental structure.

* * * * *